United States Patent [19]

Kirkemo et al.

[11] Patent Number: 4,510,251

[45] Date of Patent: Apr. 9, 1985

[54] FLUORESCENT POLARIZATION ASSAY FOR LIGANDS USING AMINOMETHYLFLUORESCEIN DERIVATIVES AS TRACERS

[75] Inventors: Curtis L. Kirkemo, Grunee; Mohammed T. Shipchandler, Libertyville, both of Ill.

[73] Assignee: Abbott Laboratories, North Chicago, Ill.

[21] Appl. No.: 440,043

[22] Filed: Nov. 8, 1982

[51] Int. Cl.³ .................. G01N 33/54; G01N 33/58; G01N 33/52; G01N 33/74
[52] U.S. Cl. .................. 436/536; 436/501; 436/800; 436/817; 549/223
[58] Field of Search .............. 436/501, 536, 537, 817, 436/800

[56] References Cited

U.S. PATENT DOCUMENTS

| | | | |
|---|---|---|---|
| 4,160,016 | 7/1979 | Ullman | 436/817 X |
| 4,420,568 | 12/1983 | Wang | 436/817 X |
| 4,450,239 | 5/1984 | Chatterton | 436/800 X |
| 4,454,232 | 6/1984 | Breglio | 436/800 X |

OTHER PUBLICATIONS

Chemical Abstracts, 90: 164293g (1979).
Kobayashi, Y. et al., Steroids, 34(7), 829–834 (Dec. 1979).

*Primary Examiner*—Sidney Marantz
*Attorney, Agent, or Firm*—James L. Wilcox

[57] ABSTRACT

This disclosure relates to a method for determining ligands in biological fluids such as serum, plasma, spinal fluid, amnionic fluid and urine, wherein a novel class of aminomethylfluorescein derivative tracer compounds are employed as reagents in fluorescence polarization immunoassays.

5 Claims, No Drawings

FLUORESCENT POLARIZATION ASSAY FOR LIGANDS USING AMINOMETHYLFLUORESCEIN DERIVATIVES AS TRACERS

BACKGROUND OF THE INVENTION

The present invention relates to a method and reagents for determining ligands in biological fluids such as serum, plasma, spinal fluid, amnionic fluid and urine. The present invention also relates to a novel class of aminomethyl-fluorescein derivatives which may be employed as reagents in fluoreacent polarization immunoassays.

Competitive binding immunoassays for measuring ligands are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody conjugate produced may be quantitively measured and is inversely proportional to the quantity of ligand in the test sample. Fluorescence polarization techniques are based on the principle that a fluorescently labeled compound when excited by linearly polarized light will emit fluorescence having a degree of polarization inversely related to its rate of rotation. Therefore, when a molecule such as a tracer-antibody conjugates having a fluorescent label is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescence polarization provides a quantitive means for measuring the amount of tracer-antibody conjugate produced in a competitive binding immunoassay.

SUMMARY OF THE INVENTION

The present invention relates to a novel class of fluorescein derivatives of the formula:

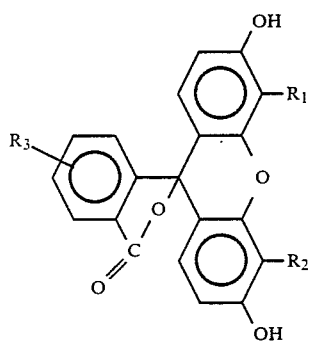

wherein
$R_1$ is a

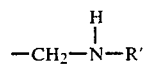

group wherein R' is hydrogen or a group represented by R" wherein R" is a ligand-analog having at least one common epitope with a ligand so as to be specifically recognizable by a common antibody;
$R_2$ is hydrogen or a group represented by $R_1$; and
$R_3$ is hydrogen, amino or carboxyl; and biologically acceptable salts thereof.

The compounds of the present invention are useful as reagents in fluorescent polarization immunoassays.

DETAILED DESCRIPTION OF THE INVENTION

The term "ligand" as used herein refers to a molecule in particular a low molecular weight hapten, to which a binding protein, normally an antibody, can be obtained or formed. Haptens are protein-free compounds, generally of low molecular weight that do not induce antibody formation when injected into an animal, but are reactive to antibodies. Antibodies to hapten are generally raised by first conjugating the haptens to a protein and injecting the conjugate product into an animal. The resulting antibodies are isolated by conventional antibody isolation techniques.

Ligands determinable by the method of the present invention vary over a wide molecular weight range. Although high molecular weight ligands may be determined, for best results, it is generally preferable to employ the methods of the present invention to determine ligands of low molecular weight, generally in a range of 50 to 4000. It is more preferred to determine ligands having a molecular weight in a range of 100 to 2000.

Representative of ligands determinable by the methods of the present invention include steroids such as estriol estrone, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid, thyroxine, triiodothyronine, histamine, serotonin, prostaglandins such as PGE, PGF, PGA: antiasthamatic drugs such as theophylline; antineoplastic drugs such as doxorubicin and methotrexate; antiarrhythmic drugs such as disopyramide, lidocaine, procainamide, propranolol, quinidine, N-acetyl procainamide; anticonvulsant drugs such a phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylates; antidepressant drugs including tricyclics such as nortriptyline, amitriptyline, imipramine and desipramine; and the like as well as the metabolites thereof. In addition, drugs of abuse such as morphine, heroin, hydromophone, oxymorphone, metapon, codeine, hydrocodone, dihydrocodiene, dihydrohydroxy codeinone, pholcodine, dextromethorphan, phenazocine and deonin and their metabolites may be determined in accordance with the methods of the present invention.

The term "ligand-analog" as used herein refers to a mono- or polyvalent radical, a substantial proportion of which has the same spatial and polar organization as the ligand to define one or more determinant or epitopic sites capable of competing with the ligand for the binding sites of a receptor. A characteristic of such ligand-analog is that it possesses sufficient structural similarity to the ligand of interest so as to be recognized by the antibody for the ligand. For the most part, the ligand analog will have the same or substantially the same structure and charge distribution (spatial and polar organization) as the ligand of interest for a significan portion of the molecular surface. Since frequently, the linking site for a hapten will be the same in preparing the antigen for production of antibodies as used for linking to the ligand, the same portion of the ligand analog which provides the template for the antibody will be exposed by the ligand analog in the tracer.

The ligand analogs may be described as functional or functionalized ligands suitable for conjugation to an aminomethylfluorescein derivative of the formula:

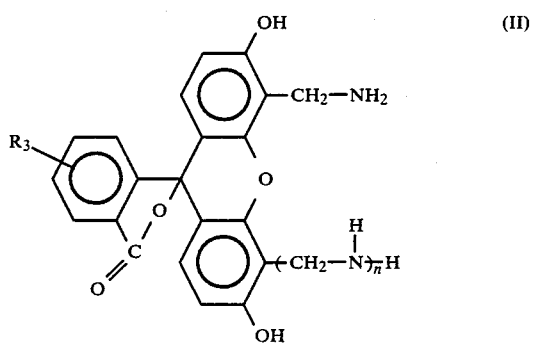

wherein n is 0 or 1.

Representative of suitable functional groups include, for example, activated acids, i.e., active esters, acid chlorides, and amides; isocyanates, isothiocyanates, and substituted haloalkyl derivatives.

The tracers of the present invention generally exist in an equilibrium between their protonated and ionized states, and in the ionized state are effective in the method of the present invention. Therefore, the present invention comprises the tracers of either the protonated or ionized state and for convenience, the tracers of the present invention are structurally represented herein in their protonated form. When the tracers of the present invention are present in their ionized state, the tracers exist in the form of biologically acceptable salts. As used herein the term "biologically acceptable salts" refers to salts such as sodium, potassium, ammonium and the like which will enable the tracers of the present invention to exist in their ionized state when employed in the method of the present invention. Generally, the tracers of the present invention exist in solution as salts, the specific salt results from the buffer employed, i.e., in the presence of a sodium phosphate buffer, the tracers of the present invention will generally exist in their ionized state as a sodium salt.

The tracers of the present invention may be prepared in accordance with the following procedure:

Fluorescein is treated with chloroacetamidomethanol in the presence of sulfuric acid to yield a chloroacetamide derivative of the formula:

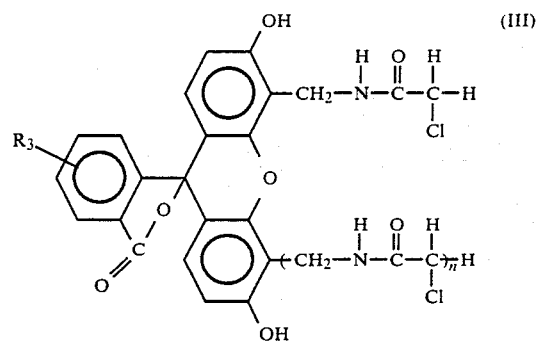

The chloroacetamide derivative is hydrolyzed in the presence of acid and ethanol to yield an acid salt of an aminomethylfluorescein of the formula:

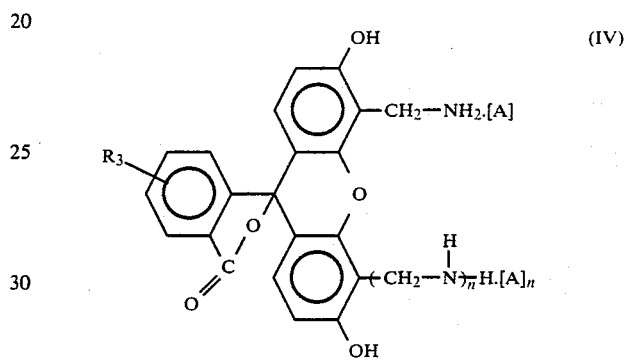

wherein A is an acid salt having a pH less than 3 such as for example, hydrochloride, trifluoroacetate, acetate, trichloroacetate, and the like.

The aminomethyl fluorescein derivative of formula (IV) is treated with an activated ester of a ligand-analog of the formula:

wherein Y is an activated ester group; in the presence of a suitable solvent to yield the compounds of the formula:

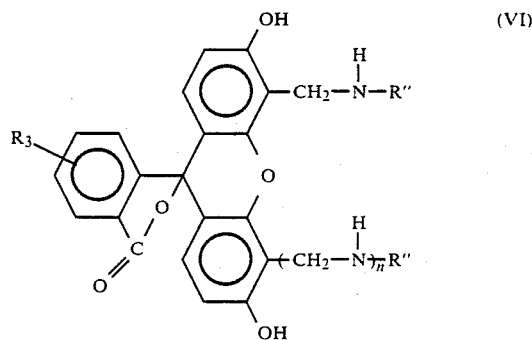

The temperature at which the reaction for preparing the tracers of this invention proceeds is not critical. The temperature should be one which is sufficient so as to initiate and maintain the reaction. Generally, for convenience and economy, room temperature is sufficient. In preparing the tracers of the present invention, the ratio of reactants is not narrowly critical.

For ease of handling and recovery of product, the process for preparing the tracers of the present invention is conducted in the presence of an inert solvent. Suitable inert solvents include those solvents which do not react substantially with the starting materials and are sufficient to dissolve the starting materials and include for example, chloroform, pyridine, and the like. In order to provide maximum product yields, the reaction preferably proceeds under neutral or basic conditions. Suitable bases include for example, triethylamine, pyridine, and the like. The reaction products are generally purified using either thin-layer or column chromatography prior to application in the methods of the present invention.

In accordance with the method of the present invention, a sample containing the ligand to be determined is intermixed with a biologically acceptable salt of a tracer of formula (VI) and an antibody specific for the ligand and tracer. The ligand present in the sample and the tracer compete for limiting antibody sites resulting in the formation of ligand-antibody and tracer-antibody complexes. By maintaining constant the concentration of tracer and antibody, the ratio of ligand-antibody complex to tracer-antibody complex that is formed is directly proportional to the amount of ligand present in the sample. Therefore, uon exciting the mixture with fluorescent light and measuring the polarization of the fluorescence emitted by a tracer and a tracer-antibody complex, one is able to quantitatively determine the amount of ligand in the sample.

In theory, the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of a ligand, the observed polarization value is closer to that of the free ligand, i.e., low. If the test sample contains a low concentration of the ligand, the polarization value is closer to that of the bound ligand, i.e., high. By sequentially exciting the reaction mixture of the immunoassay with vertically and then horizontally polarized light and analyzing only the vertical component of the emitted light, the polarization of fluorescence of the reaction mixture may be accurately determined. The precise relationship between polarization and concentration of the ligand to be determined is established by measuring the polarization values of calibrators with known concentrations. The concentration of the ligand can be extrapolated from a standard curve prepared in this manner.

The pH at which the method of the present invention is practiced must be sufficient to allow the tracers of formula (VI) to exist in their ionized state. The pH may range from about 3 to 12, more usually in the range of from 5 to 10, most preferably from about 6 to 8. Various buffers may be used to achieve and maintain the pH during the assay procedure. Representative buffers include borate, phosphate, carbonate, tris, barbital, and the like. The particular buffer employed is not critical to the present invention, but in an individual assay, a specific buffer may be preferred in view of the antibody employed and the ligand to be determined. The cation portion of the buffer will generally determine the cation portion of the tracer salt in solution.

The methods of the present invention are practiced at moderate temperatures and preferably at a constant temperature. The temperature will normally range from about 0° to 50° C., more usually from about 15° to 40° C.

The concentration of ligand which may be assayed will generally vary from about $10^{-2}$ to $10^{-3}$M, more usually from about $10^{-4}$ to $10^{-10}$M. Higher concentrations of ligand may be assayed upon dilution of the original sample.

In addition to the concentration range of ligand of interest, considerations such as whether the assay is qualitative, semiquantitative, or quantitative, the equipment employed, and the characteristics of the tracer and antibody will normally determine the concentration of the tracer and antibody to be employed. While the concentration of the other reagents, i.e., tracer and antibody, normally to optimize the sensitivity of the assay, individual reagent concentrations will be determined empirically. Concentrations of the tracer and antibody are readily ascertained by one of ordinary skill in the art.

The following illustrative, nonlimiting examples will serve to further demonstrate to those skilled in the art the manner in which specific tracers within the scope of this invention may be prepared.

EXAMPLE 1

To 5 grams (15.1 mMol) of fluorescein in 25 ml of concentrated sulfuric acid was added 1.88 grams (14.6 mMol) of chloroacetimidomethanol, with constant stirring. After 16 hours, the resulting mixture was poured into 500 ml of water. A precipitate formed and was collected by filtration. The precipitate was dissolved in a 1:1 mixture of methanol: methylene chloride. Anhydrous magnesium sulfate was added to the resulting mixture and a crude product was further purified by chromatography using a mixture of 10% methanol/10% benzene/80% methylene chloride as the eluent to yield 4.2 g (64% yield) of a chloroacetamide derivative of fluorescein of the formula:

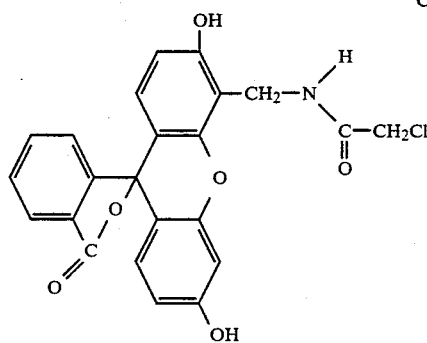

Compound 1

EXAMPLE 2

To 3 grams (6.9 mMol) of the chloroacetimide fluorescein derivative prepared in Example 1, was added 20 ml of 95% ethanol and 3 ml of concentrated hydrochloric acid. The resulting mixture was refluxed overnight and upon completion of the reaction, the resulting mixture was concentrated to yield a crude product. The crude product was purified using silica gel chromatography utilizing a 7.3 mixture of methylene chloride:methanol (7:3) as the eluent to yield 2 grams (73% yield) of a 4-aminomethylfluorescein derivative of the formula:

theophyllineaminomethylfluorescein derivative of the formula:

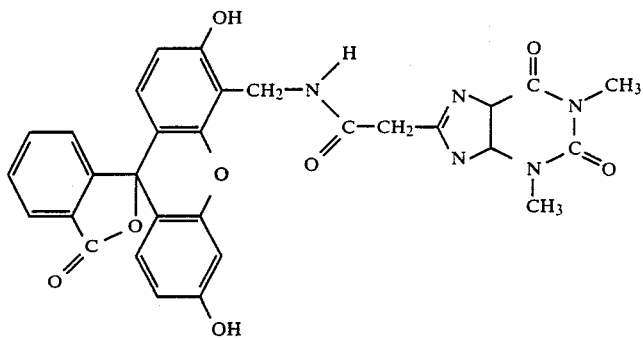

Compound 3

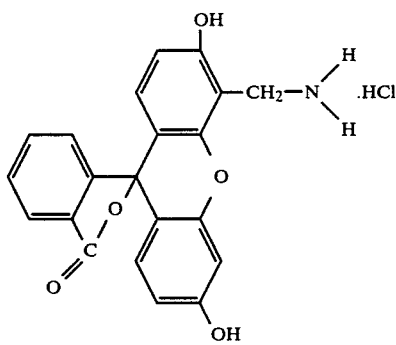

Compound 2

EXAMPLE 3

EXAMPLE 4

To 61 mg (0.14 mmol) of cortisol-3-carboxymethyloxime dissolved in 2 ml of tetrahydrofurane was added 16 mg (0.14 mmol) of N-hydroxysuccinimide and 36 mg (0.17 mmol) of dicyclohexylcarbodiimide. The reaction was allowed to proceed for three hours after which time the reaction mixture was filtered and the filtrate was added to a solution containing 50 mg (0.12 mmol) of a 4-aminomethylfluorescein derivative prepared in Example 2 in 5 ml of a 8:2 mixture of tetrahydrofuran:methanol. The resulting mixture was stirred overnight and was then concentrated to yield a crude product which was purified by preparative thin-layer chromatography utilizing a 9:1 mixture of methylene chloride:methanol to yield 25 mg (25% yield) of a cortisol-aminomethyl fluorescein derivative of the formula:

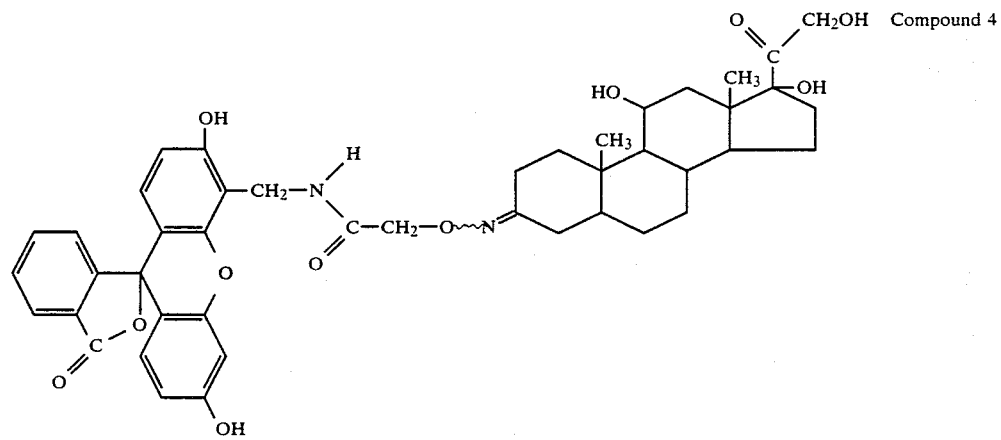

Compound 4

To 100 mg (0.4 mMol) of 8-carboxymethyl theophylline dissolved in tetrahydrofurane was added 85 mg (0.52 mMol) of carbonyldiimidizole. The reaction was allowed to proceed for 15 minutes after which time a mixture containing 151 mg (0.38 mMol) of a 4-aminomethylfluorescein derivative prepared in Example 2, in 2 ml of dimethylformamide was added to the reaction mixture. Upon completion of the reaction, the solvent was removed under vacuum to yield a crude product which was purified using preparative thin-layer chromatography employing a 15% mixture of methanol in methylene chloride to yield 120 mg (54% yield) of a

EXAMPLE 5

To a solution containing 39.4 mg (0.99 mmol) of a 4-aminomethylfluorescein derivative prepared as in Example 2 in 2 ml of dimethylformamide and 10 mg (0.99 mmol) of triethylamine was added 100 mg (0.11 mmol) of an N-hydroxysuccinimide active ester of N-acetylthyroxine. Upon completion of the reaction, 25 ml of a 2:1 mixture of ether:hexane was added to the reaction mixture and a crude product precipitated which was purified using preparative thin-layer chromatography employing an 8:1 mixture of methylene chloride:methanol:benzene to yield 50 mg (43% yield)

of a thyroxine-aminomethylfluorescein derivative of the formula:

Compound 5

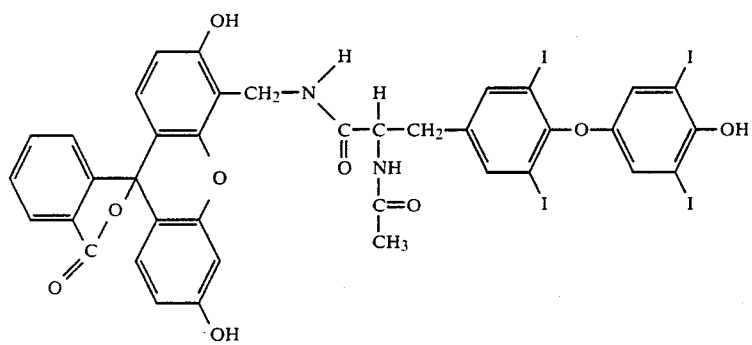

EXAMPLE 6

To a mixture containing 50 mg (0.12 mmol) of a 4-aminomethylfluorescein derivative prepared as in Example 2 in 50 ml of a 9:1 mixture of tetrahydrofurane:-dimethylformamide was added 41.4 mg (0.13 mmol) of 5-(2-chloroformylethyl)-5-phenyl barbituric acid. The reaction mixture was stirred overnight and was then concentrated under vacuum to yield a product which was purified by preparative thin-layer chromatography in a 5% mixture of methanol and methylene chloride to yield 10 mg (12% yield) of a phenylbarbitalaminomethylfluorescein derivative of the formula:

Compound 6

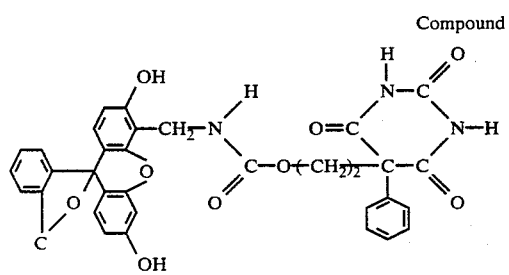

EXAMPLE 7

To 40 mg (0.11 mmol) of estriol-6-carboxymethyloxime dissolved in 1 ml of tetrahydrofurane was added 16 mg (0.14 mmol) of N-hydroxysuccinimide and 29 mg (0.14 mmol) of dicyclohexylcarbodiimide. The reaction mixture was stirred at room temperature for five hours to produce an active ester of estriol and dicyclohexylurea was removed by filtration. The active ester of estriol thus formed is added to a mixture containing 42 mg (0.11 mmol) of a 4-aminomethylfluorescein derivative prepared in Example 2 in 5 ml of a 9:1 mixture of tetrahydrofurane:methanol. The reaction mixture was stirred overnight at room temperature and solvent is removed under vacuum to yield a crude product which is purified using preparative thin-layer chromatography employing a 9:1 mixture of methylene chloride:methanol as a solvent to yield 31 mg (41% yield) of an estriol-aminomethylfluorescein derivative of the formula:

Compound 7

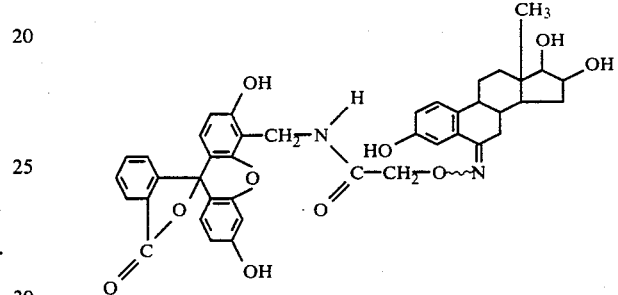

As previously mentioned, the tracers of the present invention are effective reagents for use in fluorscence polarization immunoassays. The following examples illustrate the suitability of tracers of the present invention in immunoassays employing fluorescence polarization techniques. Such assays are conducted in accordance with the following general procedure:
(1) A measured volume of standard or test serum is delivered into a test tube and diluted with buffer;
(2) A known concentration of a tracer of the present invention optionally containing a surfactant is then added to each tube;
(3) A known concentration of antisera is added to the tubes;
(4) The reaction mixture is incubated at room temperature; and
(5) The amount of tracer bound to antibody is measured by fluorescence polarization techniques as a measure of the amount of ligand in the sample.

EXAMPLE 8

Estriol Assay

A. Materials Required:
1. BGG buffer consisting of 0.1M sodium phosphate, pH 7.35, containing bovine gammaglobulin, 0.01% and sodium azide, 0.01%.
2. Tracer, consisting of estriol carboxymethyloxime aminomethylfluorescein prepared in Example 7 at a concentration of approximately 60 nM in BGG buffer.
3. Antiserum, consisting of antiserum raised against estriol diluted appropriately in BGG buffer.
4. Pretreatment solution consisting of 9M potassium thiocyanate.
5. Samples of human serum or other biological fluid containing estriol.
6. Cuvettes, 10×75 mm glass culture tubes used as cuvettes.

7. Fluorometer capable of measuring fluorescence polarization with a precision of ±0.001 units.

B. Assay Method:

1. A small volume of sample (21.6 microliters), was pipetted into a predilution container with 25 microliters of antibody solution and 25 microliters of pretreatment solution. The final volume was adjusted to approximately 500 microliters with BGG buffer.

2. 175 microliters of the above mixture in the predilution container was added to a cuvette and diluted with BGG buffer to a final volume of 0.99 ml.

3. The contents were well mixed. After three minutes, a background determination was made.

4. An additional 175 microliters of the predilution mixture was added to the assay cuvette with 25 microliters of tracer and BGG buffer to a final volume of 0.99 ml (total volume in the cuvette was approximately 2.0 ml).

5. The contents were well mixed as the volume additions were made and allowed to incubate for seven minutes.

6. The fluorescence polarization value was then determined with an appropriate instrument (fluorometer).

7. All incubations were at 35° C.

C. The results of a series of serum standards containing estriol at concentrations between 0 and 50 ng/ml are presented below.

| Concentration of Estriol (ng/ml) | Polarization |
| --- | --- |
| 0 | .310 |
| 2 | .304 |
| 5 | .299 |
| 15 | .281 |
| 30 | .250 |
| 50 | .218 |

The polarization of fluorescence is seen to decrease in a regular manner as the estriol concentration increases, allowing construction of a standard curve. Unknown samples treated in an identical manner can be quantitated by reference to the standard curve.

Using the above method, 55 unknown samples were assayed and the results correlated with a radioimmunoassay procedure using Amersham Amerlex®-Estriol (unconjugated) Estrol RIA-kit. A correlation coefficient of 0.857 was obtained.

To reduce background values in certain samples, an organic solvent extraction may be employed. The sample and 2 volumes of an appropriate organic solvent are vigorously mixed together. An aliquot of the organic solvent is removed, evaporated to dryness and resuspended. An appropriate organic solvent is ethyl acetate. BGG buffer is used for resuspension of the extracted estriol. After extraction, the resuspended material is assayed as described above.

EXAMPLE 9

Cortisol Assay

A. Materials Required:

1. BGG buffer consisting of 0.1M sodium phosphate, pH 7.5 containing bovine gamma glovulin, 0.01% and sodium azide, 0.01%.

2. Tracer, consisting of cortisol-3-carboxy-methyloxime-aminomethylfluorescein prepared in Example 4 at a concentration of approximately 80 nM in BGG buffer.

3. Antiserum, consisting of antiserum raised against cortisol diluted appropriately in BGG buffer.

4. Sample pretreatment solution, consisting of 0.5% lithium dodecyl sulfate in water.

5. Samples of human serum or other biological fluid containing cortisol.

6. Cuvettes, 10×75 mm glass culture tubes used as cuvettes.

7. Fluorometer capable of measuring fluorescence polarization with a precision of ±0.001 units.

B. Assay method:

(1) A small volume of sample was dispensed into the cuvette by pipetting 25 $\mu$l of sample and 100 $\mu$l of BGG buffer into a dilution vessel. Next, 25 $\mu$l of diluted sample was pepetted into the cuvette, followed by 25 $\mu$l of sample pretreatment solution and 950 $\mu$l of BGG buffer. After thorough mixing, the background fluorescence intensity was then read on the fluorometer.

2. Another 25 $\mu$l aliquot of diluted sample was added to the cuvette, along with 25 $\mu$l each of tracer and antibody, and 975 $\mu$l of BGG buffer. The contents are mixed thoroughly and incubated for 15 minutes at room temperature. The final equivalent sample volume in the cuvette was 10 $\mu$l.

3. The fluorescence polarization (with appropriate background subtraction) was read on the fluorometer, and a standard curve constructed to determine unknowns.

C. The results of a series of standards containing cortisol at concentrations between 0 and 60 $\mu$g/dl are presented below. Each concentration was assayed in duplicate and averaged.

| Concentration of Cortisol ($\mu$g/dl) | Polarization |
| --- | --- |
| 0 | .179 |
| 2.0 | .170 |
| 5.0 | .154 |
| 10.0 | .135 |
| 25.0 | .105 |
| 60.0 | .070 |

The polarization of fluorescence is seen to decrease in a regular manner as the cortisol concentration increases, allowing construction of a standard curve. Unknown specimens treated in an identical manner can be quantitated by reference to the standard curve. Using the above method to analyze 11 patient sera, the results obtained correlated with an HPLC reference method, Caldarella, et al, *Clin. Chem.*, 28, No. 3, page 538 (1982), with a correlation coefficient equal to 0.995.

As evident from the above results, the tracers of the present invention are effective reagents in fluorescence polarization immunoassays. In addition to the properties mentioned above, the tracers of the present invention possess a high degree of thermal stability, a high degree of bound polarization, high quantum yields and are relatively easy to produce and purify.

In addition to being useful as reagents in a fluorescence polarization immunoassay, the thyroxine aminomethylfluorescein derivatives of the present invention may be useful as tracers in a fluorescence polarization assay to determine unsaturated thyroxine binding protein sites ("T uptake") in accordance with the procedure of the following Example:

EXAMPLE 10

A. Reagents

1. Pretreatment Solution—A solution containing 0.15% sodium dodecyl sulfate 0.564M triethylenediamine (DABCO), and 0.1% sodium azide in 0.1M sodium phosphate buffer (pH. 7.25).

2. T₄—Fluorescein Tracer—Consisting of Compound 5 prepared in Example 5 is employed at a concentration of $2.4 \times 10^{-7}$M in a buffered medium containing 0.005% sodium dodecyl sulfate, 0.1% bovine gamma globulin, and 0.1% sodium azide in 0.1M sodium phosphate buffer.

3. T Uptake Calibrators—Sheep anti-T antisera in a 4% human serum matrix having the following uptake values: 0, 0.5, 1.0, 1.5, 2.0, and 2.5. An uptake value of 1.0 is equivalent to the T uptake of normal serum.

4. Diluent buffer: 0.1M sodium phosphate containing 0.1% bovine gamma globulin and 0.1% sodium azide.

All polarized fluorescence measurements were made using a polarization spectrofluorimeter (Abbott TD$_x$ ™ Fluorescence Polarization Analyzer.

B. Assay Protocol

1. To 1 μl aliquot of an unknown sample is added 25 μl of the pretreatment solution and the resulting mixture is diluted to 1 ml with diluent buffer. The resultant assay solution is mixed and the polarized fluorescence background is measured.

2. To the assay solution in Step 1. is added a second 1 μl aliquot of the unknown sample, 25 μl of the pretreatment solution 25 μl of T₄ fluorescein tracer, and the buffer to a final volume of 2 ml. The resultant solution is mixed and the polarized fluorescence is measured.

3. The fluorescence polarization due to tracer binding is obtained by subtracting the polarized fluorescence intensities of the background from the final polarized fluorescence intensities of the mixture.

4. The polarization values obtained are proportional to the T uptake of each sample.

5. The fluorescence polarization for a sample is compared to a standard curve prepared using calibrators of known T uptake values to indicate the T uptake value.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A method for determining ligands in a sample comprising intermixing with said sample a tracer of the formula:

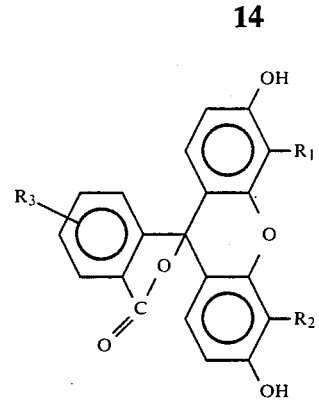

wherein
R₁ is a

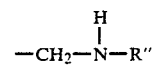

group wherein R″ is a ligand-analog having at least one common epitope with a ligand so as to be specifically recognizable by a common antibody;
R₂ is hydrogen or a group represented by R₁; and
R₃ is hydrogen, amino or carboxyl; and biologically acceptable salts thereof; and an antibody capable of specifically recognizing said ligand and said tracer; and then determining the amount of tracer bound to antibody by fluorescence polarization techniques as a measure of the amount of ligand in the sample.

2. A method according to claim 1 wherein R₂ is hydrogen.

3. A method according to claim 2 wherein R″ has a molecular weight within a range of 50 to 4000.

4. A method according to claim 3 wherein R″ is a cortisol-analog of the formula:

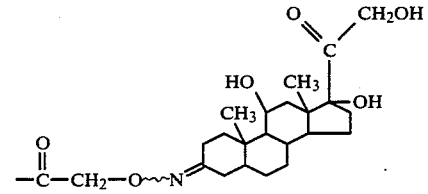

5. A method according to claim 3 wherein R″ is an estriol-analog of the formula:

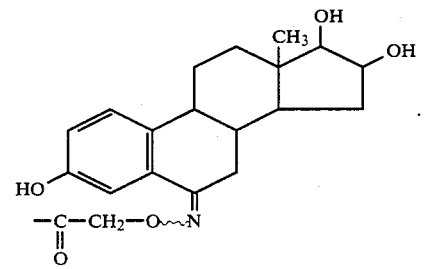

* * * * *